United States Patent [19]

Scheck

[11] Patent Number: 5,349,111
[45] Date of Patent: Sep. 20, 1994

[54] BENZOCYCLOBUTENE NOVOLAC RESIN COMPOSITIONS

[75] Inventor: Daniel M. Scheck, Midland, Mich.

[73] Assignee: The Dow Chemical Company, Midland, Mich.

[21] Appl. No.: 52,794

[22] Filed: Apr. 23, 1993

[51] Int. Cl.$^5$ .............................................. C07C 39/17
[52] U.S. Cl. .................................. 568/721; 528/129; 568/722; 568/731; 568/732; 568/744
[58] Field of Search ............... 568/722, 721, 732, 744, 568/731, 730; 528/129

[56] References Cited

U.S. PATENT DOCUMENTS

| | | | |
|---|---|---|---|
| 4,468,507 | 8/1984 | Parker | 528/491 |
| 4,474,929 | 10/1984 | Schrader | 568/722 |
| 4,701,481 | 10/1987 | Bogan et al. | 523/428 |
| 4,960,956 | 10/1990 | Wong | 568/722 |
| 4,982,014 | 1/1991 | Freitag et al. | 568/722 |
| 4,994,548 | 2/1991 | Wong | 528/219 |
| 5,079,314 | 1/1992 | Bertram et al. | 525/507 |
| 5,106,923 | 4/1992 | Bertram et al. | 525/507 |
| 5,151,496 | 9/1992 | Bertram et al. | 528/500 |

Primary Examiner—Werren B. Lone

[57] ABSTRACT

A novolac resin is prepared by reacting a phenolic compound, an aldehyde or a ketone, and a hydroxyl-substituted benzocyclobutene compound wherein the hydroxyl group is attached to an aromatic ring. The benzocyclobutenes are connected to the phenolic rings through an oxygen or oxyaryl bridge, or the cyclobutene is fused directly to a phenol ring. The novolac resin cures without evolution of volatiles and, when cured, provides a polymer which has a high glass transition temperature and which is essentially insoluble in organic solvents.

12 Claims, No Drawings

BENZOCYCLOBUTENE NOVOLAC RESIN COMPOSITIONS

BACKGROUND OF THE INVENTION

This invention relates to phenolic resins, and more particularly to novolac resin compositions.

Phenolic resins have been of commercial significance for many years and have found acceptance in a very wide range of applications. Examples of these applications include wood products (plywood, particle board, etc), insulating foams, composites, carbon—carbon composites, electrical laminates, photoresists for microlithography, resins for non-metallic honeycombs, molding compounds, and in reactive processing (RIM, pultrusion). Novolacs, the acid-catalyzed condensation products of phenols with less than 1 mole of formaldehyde per mole of phenol, constitute a well-known class of phenolic resins. They are heat stable and require a curing agent to effect polymerization. The most widely used curing agent is hexamethylenetetramine. During the curing of novolac with hexamethylenetetramine, large amounts of volatiles, predominantly ammonia, are evolved. Gas evolution during cure presents safety concerns, and also makes the fabrication of void-free moldings difficult.

Functional derivatives of phenolic resins are known which will cure without the evolution of volatiles. For example, cyanate esters of novolac resins have been cured without additives and without the evolution of volatiles. See, for example, S. Das, D. C. Prevorsek, and B. T. DeBona, *Modern Plastics*, 1990, 72; G. W. Bogan, M. E. Lyssy, G. A. Monnerat, and E. P. Woo, *SAMPE Journal*, 1988, 24 (6), 19. The synthesis of these resins requires an additional chemical step since the novolac resin must be derivatized using cyanogen bromide. Also, since the phenolic hydroxyl group is involved in the derivatization, these modified resins can no longer be considered phenolic resins. Epoxy resins, comprising the glycidyl ethers of novolac resins, are also well known in the art. Though these resins cure without evolution of volatiles, an additive, or curing agent, such as an amine, is required to effect cure. In addition, these epoxy resins display similar features to the cyanate esters described above: their synthesis requires an additional chemical step, and the reaction of the phenolic hydroxyl group results in a resin which can no longer be classified as a phenolic resin.

The condensation products of bisphenol A and chloromethylbenzocyclobutene are known, as disclosed in U.S. Pat. Nos. 4,960,956 and 4,994,548. The benzocyclobutenes are connected to the phenolic rings via a methylene bridge. The benzocyclobutene-substituted compounds are restricted to diphenolic compounds. The cured products of the resins described in these patents are moderately soluble in 1,2-dichloroethane.

It would be desirable to provide new phenolic resins which, on curing, provide polymers that have high glass transition temperatures and are essentially insoluble in organic solvents.

SUMMARY OF THE INVENTION

In a first aspect, this invention is a novolac resin which is a condensation product of a phenolic compound, an aldehyde or a ketone, and a hydroxyl-substituted benzocyclobutene compound in which the hydroxyl group is attached to an aromatic ring. The benzocyclobutenes are connected to the phenolic rings through an oxygen or oxyaryl bridge, or the cyclobutene is fused directly to a phenol ring.

The present novolac resins are mixtures of di-, tri-, tetra-, and higher oligomers in which diphenols are at most only a minor component. These resins are very similar in physical properties to conventional novolac resins which are heat stable and require an additive to effect cure. It would thus be possible for those experienced in the processing and fabrication of phenolic novolac resins to substitute the novolac resins of this invention with little modification of the equipment and processing conditions. The temperature at which the benzocyclobutene substituted novolac resins cure is significantly higher than the temperature at which they melt and flow, thus providing a convenient processing window.

In a second aspect, this invention is a process for preparing the novolac resin which comprises reacting phenol or a substituted phenolic compound, an aldehyde or a ketone, and a hydroxyl-substituted benzocyclobutene compound in which the hydroxyl group is attached to an aromatic ring.

Surprisingly, reaction conditions for the synthesis of novolac resins, which are well known in the art, are also applicable to the resins of the invention disclosed herein. Although benzocyclobutene compounds are known to be acid-sensitive and to polymerize on heating, neither the acid catalyst nor the temperatures required to remove residual phenol monomer disrupt the 4-membered ring of the benzocyclobutene to any significant extent. Thus, equipment and processing conditions familiar to manufacturers of phenolic novolac resins could be used to prepare the resins of this invention with little or no modification.

In a third aspect, this invention is a phenolic polymer derived from curing the novolac resin described above. Cure is typically accomplished thermally, at a temperature of 100° C. to 300° C., preferably at a temperature of 180° C. to 250° C. No additives are needed to effect cure, and the cured polymer can be readily prepared with no bubbles or voids. Since the mechanical properties of a polymer are seriously compromised by the presence of bubbles or voids, the invention described herein represents a significant, novel and useful modification of phenolic resin and phenolic polymer technology. The phenolic polymers of this invention derived from the cure of the benzocyclobutene-substituted novolac resins are suitable for use in a variety of applications for which phenolic novolac resins are currently used. These include, but are not limited to, composites, molding compounds, and electrical laminates.

DETAILED DESCRIPTION OF THE INVENTION

Definitions

The following terms are used in this application and have the meanings and preferred embodiments set out hereinafter unless otherwise specified.

Benzocyclobutene—Includes carbocyclic arylcyclobutene (cyclobutarene) compounds, which consist of a cyclobutene ring fused to an aromatic moiety. It will be understood that "benzocyclobutene" is an art-recognized term. In the commonly-used non-systematic numbering system for benzocyclobutenes, the 1- and 2-positions are in the cyclobutene ring. The 3- and 6-positions are in an aromatic ring, adjacent to the cyclobutene ring. The 4- and 5-positions are meta- to the cyclobutene ring. The simplest member of the series, benzocyclobutene, is formally identified as bicyclo[4.2.0]octa-1,3,5-triene. A compound, formally identified as 3-bromobicyclo[4.2.0]octa-1,3,5-triene, is commonly known as 4-bromobenzocyclobutene. The common names will be used in the specification and claims.

Aromatic moiety—Refers to carbocyclic or heterocyclic ring compound containing (4n+2)111 electrons in an orbital ring as described in Morrison & Boyd, Organic Chemistry, 3rd ed., 1973. This property is also known as resonance stabilization or delocalization.

Hydrocarbyl—Refers to any organic moiety containing only carbon and hydrogen atoms. The term hydrocarbyl means a monovalent hydrocarbon moiety including the following: alkyl, alkenyl, alkynyl, cycloalkyl, cycloalkenyl, cycloalkynyl, aryl, aliphatic and cycloaliphatic aralkyl and alkaryl, and the like.

Aliphatic—Refers to straight- and branched-, and saturated and unsaturated, hydrocarbon chains, that is, alkyl, alkenyl, or alkynyl.

Cyclo-aliphatic—Refers to saturated and unsaturated cyclic hydrocarbons, that is, cycloalkenyl, cycloalkynyl, and cycloalkyl.

Aryl—Refers to biphenyl, phenyl, naphthyl, phenanthrenyl, anthracenyl and two aryl groups bridged by an alkylene group or heteroatoms such as oxygen and sulfur.

Alkaryl—An alkyl-, alkenyl- or alkynyl-substituted aryl substituent wherein aryl is as defined hereinbefore.

Cycloalkyl—Alkyl groups containing one or more cycloaliphatic rings.

Divalent organic moiety—Any organic moiety bonded to two other moieties. The divalent organic moiety may also contain one or more heteroatoms, such as oxygen, nitrogen, phosphorus, silicon, or sulfur.

Divalent inorganic moiety—Any inorganic moiety which can bond to two other moieties. Preferred inorganic moieties include oxygen and sulfur. The most preferred inorganic moiety is oxygen.

Carbocyclic—The aromatic moiety has only carbon atoms in its nucleus. Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenylcycloalkane radicals. The most preferred carbocyclic aromatic radical is a benzene radical, which, when fused to a cyclobutene ring, produces the simplest member of the series, benzocyclobutene.

Description of the Invention

The novolac resins of this invention are represented by the following general Formulas I and II

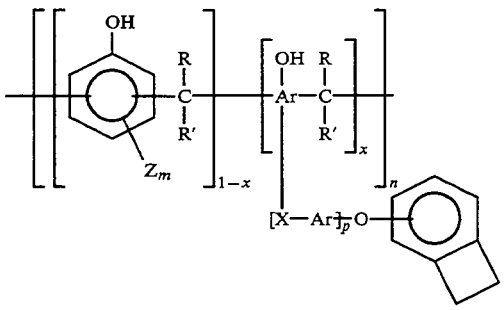

-continued

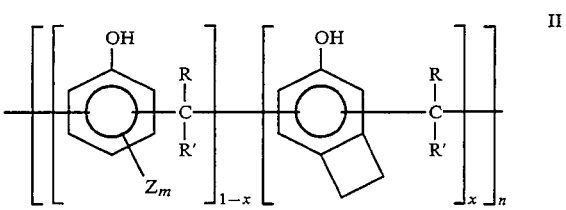

wherein:
R is independently at each occurrence hydrogen, aliphatic hydrocarbyl, aryl, aralkyl, or cycloaliphatic hydrocarbyl;
R' is independently at each occurrence hydrogen, aliphatic hydrocarbyl, aryl, aralkyl, or cycloaliphatic hydrocarbyl;
m is 0, 1, 2, or 3;
p is 0, 1, or 2;
x is 0.02 to 1.0;
n is 2 to 100;
X is a divalent organic or inorganic moiety;
Z is alkyl, aryl, or halogeno; and
Ar is independently at each occurrence a $C_6$–$C_{10}$ aromatic moiety optionally substituted with up to two groups other than hydrogen. These groups may be independently at each site $C_1$–$C_{10}$ alkyl, aryl, aralkyl, alkaryl, alkanoyl, aroyl, alkoxy, or aryloxy.

More preferably,
R is independently at each occurrence hydrogen, aliphatic hydrocarbyl, aryl, aralkyl, or cycloaliphatic hydrocarbyl;
R' is hydrogen;
m is 0, 1, or 2;
p is 0 or 1;
x is 0.05 to 0.70;
n is 2 to 30;
X is oxygen, sulfur, or an aliphatic hydrocarbyl group optionally substituted with fluorine atoms;
Z is alkyl, aryl, or halogeno; and
Ar is independently at each occurrence a $C_6$–$C_{10}$ aromatic moiety optionally substituted with $C_1$–$C_{10}$ alkyl groups.

Most preferably, the novolac resins of this invention are represented by the general Formula I, wherein:
R and R' are hydrogen;
m is 0, 1, or 2;
p is 0;
x is 0.10 to 0.40;
n is 3 to 15;
Z is an aliphatic hydrocarbyl moiety of 1 to 10 carbon atoms, halogeno, or phenyl; and
Ar is a benzene ring.

The compounds of this invention are preferably prepared by reacting a phenolic compound, an aldehyde or a ketone, and a hydroxyl-substituted benzocyclobutene compound in the presence of an acid catalyst. A typical procedure can be found in "Preparative Methods of Polymer Chemistry," W. R. Sorenson and T. L. Campbell, Wiley Interscience, second edition, 1968. The reaction can be carried out at a temperature of from about 80° C. to about 150° C., preferably from about 90° C. to about 120° C. The reaction is continued until it is essentially complete, from about 1 hour to about 8 hours, preferably from about 1.5 hours to about 3 hours. The mole ratio of aldehyde to hydroxyaromatic compounds is less than 1.0, and is adjusted to achieve the desired number average molecular weight in the product novolac resin. The term "hydroxyaromatic compounds" as used herein refers to the sum of the number of moles of the phenolic compound and the hydroxy substituted benzocyclobutene. The closer the ratio is to 1, the higher the molecular weight will be. The ratio is suitably from about 0.50 to about 0.98, preferably from about 0.7 to about 0.95. The most preferred conditions for the preparation of the compounds of this invention are set forth in the following working examples.

After the condensation is complete, the resin is isolated using standard procedures. Devolatilization to remove unreacted phenolic compound is the final step, and can be accomplished by steam distillation or by heating the resin under reduced pressure.

Suitable phenolic compounds include, but are not limited to, compounds represented by the formula shown below:

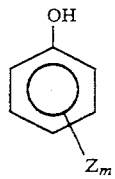

wherein Z is independently at each occurrence aryl, aliphatic hydrocarbyl group of 1 to 16 carbon atoms, preferably 1 to 4 carbon atoms, a hydroxyl group, or halogen, and m is 0, 1, 2 or 3, with the proviso that at least two of the activated positions (ortho and para to the hydroxyl group) are unsubstituted. Preferred phenolic compounds include phenol, methylphenols (cresols), dimethylphenols (xylenols), ethylphenol, propylphenol, tert-butylphenol, chlorophenol, bromophenol, resorcinol, hydroquinone, and phenylphenol. The most preferred phenolic compounds are phenol and cresol.

Suitable aldehydes include any aliphatic, cycloaliphatic or aromatic aldehyde having from 1 to about 14, preferably from 1 to about 8, carbon atoms. Particularly suitable aldehydes include, for example, formaldehyde, acetaldehyde, propionaldehyde, butyraldehyde, benzaldehyde, mixtures thereof, and the like. Most preferred aldehyde is formaldehyde.

Suitable ketones include acetone, 2-butanone, and acetophenone. Preferred ketones are acetone and 2-butanone. The most preferred ketone is acetone.

Suitable hydroxyl-substituted benzocyclobutene compounds include 4-hydroxybenzocyclobutene and 3-hydroxybenzocyclobutene.

Other suitable hydroxyl-substituted benzocyclobutene compounds include, but are not limited to, compounds represented by the formula shown below:

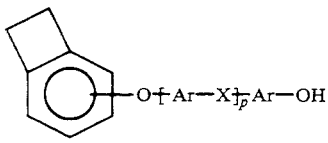

wherein Ar is independently at each occurrence a $C_6$–$C_{10}$ aromatic hydrocarbyl moiety. Each of the aromatic hydrocarbyl moieties can be optionally substituted with up to two groups other than hydrogen. These substituents may be $C_1$–$C_{10}$ alkyl, aryl, aralkyl, alkaryl, alkanoyl, aroyl, alkoxy, and aryloxy, with the proviso that, on the aromatic ring bearing the hydroxyl group, at least two activated positions (ortho or para to the hydroxyl group) are unsubstituted. Most preferably, the aromatic moieties are unsubstituted. The preferred aryl moiety bonded to the hydroxyl group is a benzene ring. The linking group X can be $C_1$–$C_8$ aliphatic hydrocarbyl group, sulfur, or oxygen. The preferred linking group is oxygen.

A process for preparing these hydroxyl-substituted benzocyclobutene compounds, such as 4-(3-hydroxyphenoxy)benzocyclobutene, is described in copending application U.S. Ser. No. 998,495, filed on Dec. 30, 1992, incorporated herein by reference.

Suitable catalysts include oxalic acid, sulfuric acid, benzenesulfonic acid, p-toluenesulfonic acid, methanesulfonic acid, and the like. The most preferred catalyst is oxalic acid.

The present invention is illustrated in further detail by the following examples. The examples are for the purposes of illustration only, and are not to be construed as limiting the scope of the present invention. All parts and percentages are by weight unless otherwise specifically noted.

EXAMPLE 1

A. Synthesis of phenol/4-(3-hydroxyphenoxy)benzocyclobutene novolac resin (formaldehyde:hydroxyaromatic ratio=0.83; 20 mole % benzocyclobutene)

Phenol (41.56 g, 0.442 moles), 4-(3-hydroxyphenoxy)benzocyclobutene (23.43 g, 0.110 moles), water (5 mL), aqueous formaldehyde (34.1 mL, 36.9 g of a 37% solution, 13.7 g formaldehyde, 0.455 moles), and oxalic acid dihydrate (0.40 g, 0.0044 moles) are combined in a 250 mL resin flask. The flask is equipped with a reflux condenser, nitrogen inlet, air driven overhead stirrer, and thermometer. The system is flushed with a stream of nitrogen and the mixture is heated to reflux and refluxed for one hour. The mixture is cooled slightly, and another 0.40 g of oxalic acid dihydrate is added. The mixture is refluxed for another hour. Water (140 mL) is added to the flask and the mixture is allowed to settle and cool. The flask is opened and the aqueous layer is poured out. Water (100 mL) is then added to the flask, and the reflux condenser is replaced with a short path distillation head. Most of the water is distilled out at atmospheric pressure. The flask is then disassembled and the warm resin is poured onto a non-stick baking sheet. The sheet is placed in a vacuum oven and the resin is dried at 110° C. at 0.5 mm Hg for 1.5 hours. The sheet is removed from the oven and allowed to cool, affording a clear, light orange brittle solid. The yield is 57.79 g. DSC shows a polymerization exotherm of 172 Joules/gram, with an exotherm peak at 264° C. Size exclusion chromatographic (SEC) analysis shows a number average molecular weight (Mn) of 760, a weight average molecular weight (Mw) of 3580, and a polydispersity index (Mw/Mn) of 4.7. Gas chromatographic (GC) analysis shows the presence of phenol monomer. The resin is placed in a 500 mL flask and is devolatilized under vacuum (0.3 mm Hg) at 100° C. for 1.5 hours and at 150° C. for 0.75 hours. The resin is allowed to cool, and is broken into small pieces and removed from the flask. GC analysis shows less than 0.02 percent phenol monomer remaining.

B. Curing of phenol/4-(3-hydroxyphenoxy)benzocyclobutene novolac resin (formaldehyde:hydroxyaromatic ratio=0.83; 20 mole % benzocyclobutene)

A mold consisting of polished stainless steel plates, 4.5"×3.5"×0.125", is assembled. The inside (polished) surfaces of the mold plates are treated with fluorocarbon mold release agent. An aluminum spacer, 0.125" thick, and a rubber gasket, are placed between the plates, which are clamped together. An aluminum foil funnel is placed on top of the mold, and novolac resin prepared in Example 1a (9.5 g) is placed in this funnel. The mold is placed in an oven at 150° C. for one hour to allow the resin to flow into the mold. The resin is then cured according to the following cure schedule: one hour at 180° C.; one hour at 200° C.; one hour at 220° C.; one hour at 250° C. The mold is allowed to cool to room temperature. The mold is opened and a hard, solid, light orange-brown, void-free molding is obtained. The weight of the molding is 9.1 g, and the dimensions of the molding are 2.625"×1.5"×0.125". The molding is cut into test specimens and characterized by differential scanning calorimetry (DSC), thermogravimetric analysis (TGA), thermal mechanical analysis (TMA), and dynamic mechanical spectroscopy (DMS). The data are summarized in Table 1.

EXAMPLE 2

A. Synthesis of phenol/4-(3-hydroxyphenoxy)benzocyclobutene novolac resin (formaldehyde:hydroxyaromatic ratio=0.92; 20 mole % benzocyclobutene)

Phenol (25.97 g, 0.276 moles), 4-(3hydroxyphenoxy)benzocyclobutene (14.70 g, 0.069 moles), water (3 mL), oxalic acid dihydrate (0.50 g, 0.004 moles), and aqueous formaldehyde (23.8 mL, 25.7 g of a 37% solution, 9.52 g of formaldehyde, 0.317 moles) are combined in a 100 mL resin flask. The flask is equipped with an air driven overhead stirrer, reflux condenser, nitrogen inlet, and thermometer. The system is flushed with a stream of nitrogen, and the mixture is heated to reflux and refluxed for 2 hours. Water (100 mL) is then added, and the mixture is stirred for a few minutes, then allowed to settle and cool. The resin flask is disassembled and the water is poured out. The resin is transferred to a 500 mL flask and is devolatilized under vacuum at 100° C. for 1 hour and 150° C. for 1 hour. The resin is allowed to cool to ambient temperature, and the brittle light orange solid is broken up and removed from the flask. The yield is 34.20 g. GC analysis shows the presence of about 0.1% phenol monomer remaining. DSC analysis shows a glass transition temperature of 84° C., and a polymerization exotherm of Joules/gram, with an exotherm peak at 263° C. SEC analysis shows that the resin has a number average molecular weight of 1235, a weight average molecular weight of 7450, and a polydispersity index of 6.03. $^1$H-NMR analysis shows broad resonances, which are entirely consistent with the novolac structure as assigned.

B. Curing of phenol/4-(3-hydroxyphenoxy)benzocyclobutene novolac resin (formaldehyde:hydroxyaromatic ratio=0.92; 20 mole % benzocyclobutene)

Polymerization is done in accordance with the procedure of Example 1B except as follows:
1. The novolac resin prepared by the method of Example 2A (10.40 g) is used.
2. The mold is placed in the oven at 160° C. for 1.5 hours to allow the resin to flow into the mold.
3. A hard, solid, light brown, essentially void-free molding is obtained.

The molding is cut into test specimens and characterized by DSC, TGA, TMA and DMS. The data are summarized in Table 1.

EXAMPLE 3

A. Synthesis of phenol/4-(3-hydroxyphenoxy)benzocyclobutene novolac resin (formaldehyde:hydroxyaromatic ratio=0.83; 30 mole % benzocyclobutene)

Phenol (13.65 g, 0.145 moles), 4-(3-hydroxyphenoxy)benzocyclobutene (13.18 g, 0.0621 moles), water (2 mL), oxalic acid dihydrate (0.30 g, 0.0024 moles), and aqueous formaldehyde (12.8 mL of a 37% solution, 13.9 g of solution, 5.13 g of formaldehyde, 0.171 moles) are combined in a 100 mL resin flask. The flask head is equipped with an air driven overhead stirrer, reflux condenser, nitrogen inlet, and thermometer. The system is flushed briefly with a stream of nitrogen, and the reaction mixture is heated to reflux and refluxed for 2 hours. Water (60 mL) is added to the flask, and the mixture is allowed to settle and cool. The resin flask is disassembled and the water is poured out. The crude resin is transferred to a 500 mL flask. It is devolatilized under vacuum at 100° C. for 1.5 hours and 150° C. for 1 hour. It is then cooled, broken into small pieces, and removed from the flask. The yield is 21.25 g. GC analysis shows only a trace of phenol monomer remaining (less than 0.1%). DSC analysis shows a glass transition temperature of 79° C., and a polymerization exotherm of 303 Joules/gram, with an exotherm peak at 263° C. SEC analysis shows that the resin has a number average molecular weight of 1100, a weight average molecular weight of 2290, and a polydispersity index of 2.08. $^1$H-NMR analysis shows broad resonances, which are entirely consistent with the novolac structure as assigned.

B. Curing of phenol/4-(3-hydroxyphenoxy)benzocyclobutene novolac resin (formaldehyde:hydroxyaromatic ratio=0.83; 30 mole % benzocyclobutene)

Polymerization is done in accordance with the procedure of Example 1B except as follows:
1. The novolac resin prepared by the method of Example 3A (11.6 g) is used.
2. The mold is placed in the oven at 160° C. for 1.25 hours to allow the resin to flow into the mold.
3. A hard, solid, light brown, essentially void-free molding is obtained.
4. The dimensions of the molding are 3.25"×1.125"×0.125".

The molding is cut into test specimens and characterized by DSC, TGA, TMA and DMS. The data are summarized in Table 1.

C. Solvent and moisture resistance of phenolic polymer

A polymer part is prepared as described in Example 3B and the part is cut into pieces. The pieces are weighed and immersed in water (at reflux) and various organic solvents (at room temperature). After 7 days the polymer pieces are removed from the liquids, wiped dry, and reweighed. No swelling, change in appearance, or appreciable dissolution of the pieces is observed. The solvents used and weight changes observed after 7 days are recorded in Table 2.

EXAMPLE 4

A. Synthesis of phenol/4-(3-hydroxyphenoxy)benzocyclobutene novolac resin (formaldehyde:hydroxyaromatic ratio=0.83; 40 mole % benzocyclobutene)

Phenol (7.80 g, 0.083 moles), 4-(3-hydroxyphenoxy)benzocyclobutene (11.72 g, 0.055 moles), water (1.3 mL), aqueous formaldehyde (8.5 mL of a 37% solution, 9.2 g of solution, 3.41 g of formaldehyde, 0.113 moles), and oxalic acid dihydrate (0.10 g, 0.0008 moles) are combined in a 100 mL resin flask. The flask is equipped with a reflux condenser, nitrogen inlet, overhead stirrer, and thermometer. The system is flushed with a stream of nitrogen and the mixture is heated to reflux. After one hour at reflux an additional 0.10 g oxalic acid dihydrate (0.0008 moles) is added. Reflux is continued for another hour. Water (40 mL) is then added and the mixture is allowed to settle and cool. The water layer is poured off, and the resin is transferred to a 250 mL flask and devolatilized under vacuum (0.3 mm Hg) at 100° C. for 1 hour and at 150° C. for 0.75 hours. The resin is allowed to cool, and the light orange solid is broken into small pieces and removed from the flask. The $^1$H- and $^{13}$C-NMR spectra are entirely consistent with the novolac structure as assigned. DSC analysis shows a glass transition temperature of 83° C. and a polymerization exotherm of 274 Joules/gram, with the exotherm peak occurring at 262° C. SEC analysis shows a number average molecular weight of 1010, a weight average molecular weight of 2180, and a polydispersity index of 2.16. GC analysis shows the presence of approximately 0.3% phenol monomer. The resin is further devolatilized under vacuum at 150°–160° C. for one hour. GC analysis at this point shows the residual phenol monomer content to be less than 0.1%.

B. Curing of phenol/4-(3-hydroxyphenoxy)benzocyclobutene novolac resin (formaldehyde:hydroxyaromatic ratio=0.83; 40 mole % benzocyclobutene)

Polymerization is done in accordance with the procedure of Example 1B except as follows:

1. The novolac resin prepared by the method of Example 4A (9.0 g) is used.
2. The mold is placed in the oven at 160° C. for one hour to allow the resin to flow into the mold.
3. A hard, solid, brown polymer part is obtained. The part has no bubbles voids, or cracks.

The molding is cut into test specimens and characterized by DSC, TGA and TMA. The data are summarized in Table 1.

EXAMPLE 5

A. Synthesis of p-cresol/4-(3-hydroxyphenoxy)benzocyclobutene novolac resin (formaldehyde:hydroxyaromatic ratio=0.83; 20 mole % benzocyclobutene)

p-Cresol (35.52 g, 0.329 moles), 4-(3-hydroxyphenoxy)benzocyclobutene (17.88 g, 0.084 moles), water (4 mL), aqueous formaldehyde (25.5 mL of a 37% solution, 27.6 g of solution, 10.22 g of formaldehyde, 0.340 moles), and oxalic acid dihydrate (0.30 g, 0.0024 moles) are combined in a 250 mL resin flask. The flask is equipped with a reflux condenser, nitrogen inlet, air driven overhead stirrer, and thermometer. The system is flushed with a stream of nitrogen, and the mixture is heated to reflux. After one hour at reflux the mixture is cooled slightly and another 0.30 g (0.0024 moles) of oxalic acid dihydrate is added. Reflux is resumed and is continued for another hour. Water (90 mL) is then added and the mixture is allowed to settle and cool. The resin flask is opened, the water is poured out, and the resin is poured onto a non-stick baking sheet. The resin is dried under vacuum at 100° C. for 1.5 hours. The yield of resin is 44.22 g. The $^1$H- and $^{13}$C-NMR spectra are entirely consistent with the novolac structure as assigned. DSC analysis shows a polymerization exotherm of 204 Joules/gram with the exotherm peak occurring at 264° C. SEC analysis shows a number average molecular weight of 530, a weight average molecular weight of 3250, and a polydispersity index of 6.15. GC analysis, as well as the NMR and SEC analyses, show the presence of p-cresol monomer. The resin is placed in a 250 mL flask and is devolatilized under vacuum at 100° C. for 1.5 hours and at 150° C. for 0.75 hours. The resin is allowed to cool, and is broken into small pieces and removed from the flask. GC analysis shows that the residual p-cresol monomer content is about 0.2%.

B. Curing of p-cresol/4-(3-hydroxyphenoxy)benzocyclobutene novolac resin (formaldehyde:hydroxyaromatic ratio=0.83; 20 mole % benzocyclobutene)

A mold consisting of polished stainless steel plates, 4.5"×3.5"×0.125", is assembled. The inside (polished) surfaces of the mold plates are treated with fluorocarbon mold release agent. An aluminum spacer, 0.125" thick, and a rubber gasket, are placed between the plates, which are clamped together. The inside dimensions of the mold are 3.5"×1.25"×0.125". The mold is preheated to 160° C. in an oven. The novolac resin of Example 5A (7.4 g) is placed in a beaker and is heated to 160° C. in an oven. The hot resin is poured into the mold, and is then cured according to the following cure schedule: one hour at 180° C.; one hour at 200° C.; one hour at 220° C.; one hour at 250° C. The mold is allowed to cool to room temperature. The mold is opened and a hard, solid, light brown polymer part is removed. The dimensions of the part are 1.75"×1.25"×0.125". The part has no bubbles, voids, or cracks. The molding is cut into test specimens and characterized by DSC, TGA, and TMA. The data are summarized in Table 1.

TABLE 1

Thermal and mechanical properties of cured phenolic compund/4-(3-hydroxyphenoxy)benzocyclobutene novolac resins

| Example | phenolic compound | BCB mole %[1] | F/P[2] | Tg[3] (DSC) | TG (TMA) | TG (DMS) | char yield[4] (%) |
|---|---|---|---|---|---|---|---|
| 1 | phenol | 20 | 0.83 | 131 | 125 | 141 | 60.4 |
| 2 | phenol | 20 | 0.92 | 157 | 150 | 163 | 57.6 |
| 3 | phenol | 30 | 0.83 | 225 | 206 | 200 | 61.0 |
| 4 | phenol | 40 | 0.83 | N.D. | 243 | N.D. | 62.6 |
| 5 | p-cresol | 20 | 0.83 | 142 | 152 | N.D. | 53.9 |

[1]Ratio of the number of moles of hydroxyl substituted benzocyclobutene compound to the sum of the number of moles of hydroxyl-substituted benzocyclobutene compound and the number of moles of phenolic compund.
[2]Ratio of the number of moles of formaldehyde to the sum of the number of moles of hydroxyl-substituted benzocyclobutene compound and the number of moles of phenolic compound.
[3]Glass transition temperature in degrees Centigrade, as determined by differential scanning calorimetry (DSC), thermal mechanical analysis (TMA), and dynamic mechanical spectroscopy (DMS). The Tg by DMS is the maximum in the loss modulus (G") curve.
[4]Percentage of weight remaining in a thermogravimetric experiment after heating to 800° C. under nitrogen at a rate of 10° C. per minute.
N.D. Not determined

TABLE 2

Moisture and organic solvent uptake of cured phenol/4-(3-hydroxyphenoxy)benzocyclobutene novolac resin (from Example 3B)

| Solvent | Weight change (7 days) |
|---|---|
| water | +3.23% |
| methanol | +3.3% |
| toluene | +0.27% |
| methylene chloride | +0.24% |
| ethylene glycol | −0.09% |
| 2-butanone | +0.02% |

The water uptake test is conducted in boiling water. All the other solvent resistance tests are conducted at room temperature.

What is claimed is:

1. A compound represented by the formula

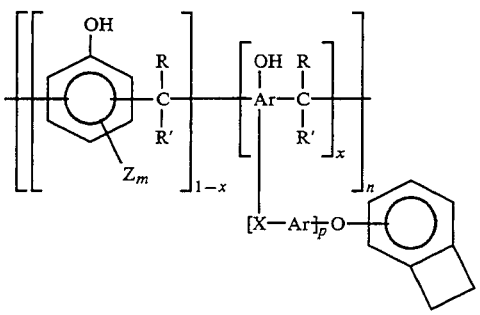

wherein:
R is independently at each occurrence hydrogen, aliphatic hydrocarbyl, aryl, aralkyl, or cycloaliphatic hydrocarbyl;
R' is independently at each occurrence hydrogen, aliphatic hydrocarbyl, aryl, aralkyl, or cycloaliphatic hydrocarbyl;
m is 0, 1, 2 or 3;
p is 0, 1, or 2;
x is 0.02 to 1.0;
n is 2 to 100;
X is a divalent organic or inorganic moiety;
Z is alkyl, aryl or halogeno; and
Ar is independently at each occurrence a $C_6$–$C_{10}$ aromatic moiety.

2. The compound of claim 1, wherein:
R is independently at each occurrence hydrogen, aliphatic hydrocarbyl, aryl, aralkyl, or cycloaliphatic hydrocarbyl;
R' is hydrogen;
m is 0, 1, or 2;
p is 0 or 1;
x is 0.05 to 0.70;
n is 2 to 30;
X is oxygen, sulfur, or an aliphatic hydrocarbyl group;
Z is alkyl, aryl, or halogeno; and
Ar is a $C_6$–$C_{10}$ aromatic moiety.

3. The compound of claim 1, wherein:
R and R' are hydrogen;
m is 0, 1, or 2;
p is 0;
x is 0.10 to 0.40;
n is 3 to 15;
Z is an aliphatic hydrocarbyl moiety of 1 to 10 carbon atoms, halogeno, or phenyl; and
Ar is a benzene ring.

4. The compound of claim 3 wherein m is 0.

5. The compound of claim 3 wherein Z is a methyl group and m is 1.

6. The compound of claim 3 wherein Z is chloro and m is 1.

7. The compound of claim 1 wherein Ar is independently at each occurrence a $C_6$–$C_{10}$ aromatic moiety substituted with a $C_1$–$C_{10}$ alkyl, aryl, aralkyl, alkaryl, alkanol, aroyl, alkoxy, or aryloxy.

8. The compound of claim 3 wherein X is an aliphatic hydrocarbyl group substituted with fluorine atoms.

9. The compound of claim 3 wherein Ar is a $C_6$–$C_{10}$ aromatic moiety substituted with a $C_1$–$C_{10}$ alkyl group.

10. A compound represented by the formula:

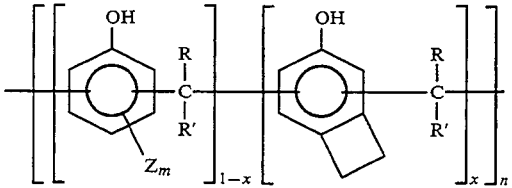

wherein:
R is independently at each occurrence hydrogen, aliphatic hydrocarbyl, aryl, aralkyl, or cycloaliphatic hydrocarbyl;
R' is independently at each occurrence hydrogen, aliphatic hydrocarbyl, aryl, aralkyl, or cycloaliphatic hydrocarbyl;
m is 0, 1, 2 or 3;
x is 0.02 to 1.0;
n is 2 to 100; and
Z is alkyl, aryl, or halogeno.

11. The compound of claim 10 wherein R and R' are hydrogen.

12. A process for preparing the compound of claim 2 which comprises reacting a phenolic compound, an aldehyde or a ketone, and a hydroxyl-substituted benzocyclobutene compound, in the presence of an acid catalyst selected from the group consisting of oxalic acid, sulfuric acid, benzenesulfonic acid, p-toluenesulfonic acid and methanesulfonic acid.

* * * * *